US012692312B2

(12) United States Patent
Zhou et al.

(10) Patent No.: US 12,692,312 B2
(45) Date of Patent: Jul. 28, 2026

(54) CD7-TARGETING HUMANIZED ANTIBODY AND USE THEREOF

(71) Applicant: BIOHENG THERAPEUTICS LIMITED, Grand Cayman (KY)

(72) Inventors: Yali Zhou, Nanjing (CN); Xiaoyan Jiang, Nanjing (CN); Gong Chen, Nanjing (CN); Jiangtao Ren, Nanjing (CN); Xiaohong He, Nanjing (CN); Yanbin Wang, Nanjing (CN); Lu Han, Nanjing (CN)

(73) Assignee: BIOHENG THERAPEUTICS LIMITED, Grand Cayman (KY)

( * ) Notice: Subject to any disclaimer, the term of this patent is extended or adjusted under 35 U.S.C. 154(b) by 601 days.

(21) Appl. No.: 18/034,170

(22) PCT Filed: Oct. 29, 2021

(86) PCT No.: PCT/CN2021/127570
§ 371 (c)(1),
(2) Date: Apr. 27, 2023

(87) PCT Pub. No.: WO2022/095803
PCT Pub. Date: May 12, 2022

(65) Prior Publication Data
US 2023/0399398 A1 Dec. 14, 2023

(30) Foreign Application Priority Data

Nov. 3, 2020 (CN) .......................... 202011208669.1

(51) Int. Cl.
| | |
|---|---|
| *C07K 16/28* | (2006.01) |
| *A61K 35/17* | (2015.01) |
| *A61K 40/31* | (2025.01) |
| *A61P 35/00* | (2006.01) |
| *C07K 14/705* | (2006.01) |
| *C12N 15/63* | (2006.01) |

(52) U.S. Cl.
CPC .......... *C07K 16/2803* (2013.01); *A61K 35/17* (2013.01); *A61K 40/31* (2025.01); *A61P 35/00* (2018.01); *C07K 14/70521* (2013.01); *C12N 15/63* (2013.01); *C07K 2317/24* (2013.01); *C07K 2317/31* (2013.01); *C07K 2317/565* (2013.01)

(58) Field of Classification Search
CPC ................................................. C07K 16/2803
See application file for complete search history.

(56) References Cited

U.S. PATENT DOCUMENTS

2013/0156786 A1 6/2013 Corvey et al.

FOREIGN PATENT DOCUMENTS

| | | |
|---|---|---|
| CN | 107849123 A | 3/2018 |
| CN | 109652379 A | 4/2019 |
| CN | 110268049 A | 9/2019 |
| CN | 111196852 A | 5/2020 |
| CN | 112300282 A | 2/2021 |
| WO | 2017213979 A1 | 12/2017 |
| WO | 2018098306 A1 | 5/2018 |
| WO | 2020102589 A1 | 5/2020 |

OTHER PUBLICATIONS

EPO Search Report of counterpart European application No. 21888500, dated Apr. 24, 2024.
NPL cited in OA1 of JP 2023-524926.
NPL cited in OA2 of JP 2023-524926.
OA1 of counterpart European application No. 21888500, dated May 7, 2024.
OA1 of counterpart Japanese application No. 2023-524926, dated Apr. 9, 2024, with EN translation.
OA1 of counterpart Korean application No. 10-2023-7012746, dated Oct. 13, 2025, with EN translation.
OA2 of counterpart Japanese application No. 2023-524926, dated Sep. 17, 2024, with EN translation.
Pauza M E et al: "Construction and characterization of human CD7-specific single-chain Fv immunotoxins.", The Journal of Immunology, vol. 158, No. 7, Apr. 1, 1997 (Apr. 1, 1997), US, pp. 3259-3269, XP093150825, ISSN: 0022-1767, Retrieved from the Internet DOI: 10.4049/jimmunol.158.7.3259 [I] 1-13 p. 3259, col. r, paragraph 2 p. 3260, col. r, paragraph 2; figure 8; table 1.
Yu Yuan et al: "Humanized CD7 nanobody-based immunotoxins exhibit promising anti-T-cell acute lymphoblastic leukemia potential", International Journal of Nanomedicine, vol. vol. 12, Mar. 1, 2017 (Mar. 1, 2017), pp. 1969-1983, XP093097885, Retrieved from the Internet DOI: 10.2147/IJN.S127575 [A] 1-13 the whole document.
English translation of ISR of WO2022095803.
English translation of OA1 of priority application of CN202011208669. 1.
First search of priority application CN202011208669.1.
International Search Report of WO2022095803.
OA1 of priority application of CN202011208669.1.
OA2 of priority application of CN202011208669.1.
SFv antibody, partial [Mus musculus]—Protein—NCBI.
Written Opinion of The International Searching Authority of WO2022095803.

*Primary Examiner* — Prema M Mertz

(74) *Attorney, Agent, or Firm* — Platinum Intellectual Property PC

(57) ABSTRACT

The present invention provides a CD7-targeting humanized antibody, and a multispecific antibody, chimeric antigen receptor, antibody conjugate, pharmaceutical composition, and kit comprising the CD7-targeting humanized antibody, and a use thereof in the diagnosis/treatment/prevention of diseases associated with CD7 expression.

9 Claims, 2 Drawing Sheets

Specification includes a Sequence Listing.

T cell toxicity

IFN-γ

SEQUENCE LISTING

<160> NUMBER OF SEQ ID NOS: 45

<210> SEQ ID NO 1
<211> LENGTH: 11
<212> TYPE: PRT
<213> ORGANISM: Artificial Sequence
<220> FEATURE:
<223> OTHER INFORMATION: CDR-L1

<400> SEQUENCE: 1

Arg Ala Ser Gln Ser Ile Ser Asn Asn Leu His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Ser Ala Ser Gln Ser Ile Ser
1               5

<210> SEQ ID NO 3
<211> LENGTH: 9
<212> TYPE: PRT
<213> ORGANISM: Artificial Sequence
<220> FEATURE:
<223> OTHER INFORMATION: CDR-L3

<400> SEQUENCE: 3

Gln Gln Ser Asn Ser Trp Pro Tyr Thr
1               5

<210> SEQ ID NO 4
<211> LENGTH: 7
<212> TYPE: PRT
<213> ORGANISM: Artificial Sequence
<220> FEATURE:
<223> OTHER INFORMATION: CDR-H1

<400> SEQUENCE: 4

Gly Tyr Thr Phe Thr Ser Tyr
1               5

<210> SEQ ID NO 5
<211> LENGTH: 6
<212> TYPE: PRT
<213> ORGANISM: Artificial Sequence
<220> FEATURE:

<223> OTHER INFORMATION: CDR-H2

<400> SEQUENCE: 5

Asn Pro Ser Asn Gly Arg
1               5

<210> SEQ ID NO 6
<211> LENGTH: 14
<212> TYPE: PRT
<213> ORGANISM: Artificial Sequence
<220> FEATURE:
<223> OTHER INFORMATION: CDR-H3

<400> SEQUENCE: 6

Gly Gly Val Tyr Tyr Asp Leu Tyr Tyr Tyr Ala Leu Asp Tyr
1               5                   10

<210> SEQ ID NO 7
<211> LENGTH: 249
<212> TYPE: PRT
<213> ORGANISM: Artificial Sequence
<220> FEATURE:
<223> OTHER INFORMATION: m189

<400> SEQUENCE: 7

Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Ser Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Gln Glu Ser Gly Ala Glu Leu Val Lys Pro Gly Ala Ser Val
        130                 135                 140

Lys Leu Ser Cys Lys Ala Ser Gly Tyr Thr Phe Thr Ser Tyr Trp Met
145                 150                 155                 160

His Trp Val Lys Gln Arg Pro Gly Gln Gly Leu Glu Trp Ile Gly Lys
                165                 170                 175

Ile Asn Pro Ser Asn Gly Arg Thr Asn Tyr Asn Glu Lys Phe Lys Ser
            180                 185                 190

Lys Ala Thr Leu Thr Val Asp Lys Ser Ser Ser Thr Ala Tyr Met Gln
        195                 200                 205

Leu Ser Ser Leu Thr Ser Glu Asp Ser Ala Val Tyr Tyr Cys Ala Arg
        210                 215                 220

Gly Gly Val Tyr Tyr Asp Leu Tyr Tyr Tyr Ala Leu Asp Tyr Trp Gly
225                 230                 235                 240

Gln Gly Thr Thr Val Thr Val Ser Ser
            245

<210> SEQ ID NO 8
<211> LENGTH: 108
<212> TYPE: PRT
<213> ORGANISM: Artificial Sequence
<220> FEATURE:
<223> OTHER INFORMATION: h189-1 VL

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Tyr
                85                  90                  95

Thr Phe Gly Gln Gly Thr Lys Val Glu Ile Lys Arg
            100                 105
```

<210> SEQ ID NO 9
<211> LENGTH: 123
<212> TYPE: PRT
<213> ORGANISM: Artificial Sequence
<220> FEATURE:
<223> OTHER INFORMATION: h189-1 VH

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120
```

<210> SEQ ID NO 10
<211> LENGTH: 249
<212> TYPE: PRT
<213> ORGANISM: Artificial Sequence
<220> FEATURE:
<223> OTHER INFORMATION: h189-1 scFv

<400> SEQUENCE: 10

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30
```

```
Leu His Trp Tyr Gln Gln Lys Pro Gly Gln Ala Pro Arg Leu Leu Ile
        35                  40                  45

Tyr Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Tyr
                85                  90                  95

Thr Phe Gly Gln Gly Thr Lys Val Glu Ile Lys Arg Gly Ser Thr Ser
                100                 105                 110

Gly Ser Gly Lys Pro Gly Ser Gly Glu Gly Ser Thr Lys Gly Gln Val
            115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Tyr Met
145                 150                 155                 160

His Trp Val Arg Gln Ala Pro Gly Gln Gly Leu Glu Trp Met Gly Trp
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
            195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245
```

<210> SEQ ID NO 11
<211> LENGTH: 108
<212> TYPE: PRT
<213> ORGANISM: Artificial Sequence
<220> FEATURE:
<223> OTHER INFORMATION: h189-2 VL

<400> SEQUENCE: 11

```
Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Val Glu Ile Lys Arg
                100                 105
```

<210> SEQ ID NO 12
<211> LENGTH: 123
<212> TYPE: PRT
<213> ORGANISM: Artificial Sequence -continued

```
<220> FEATURE:
<223> OTHER INFORMATION: h189-2 VH

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120

<210> SEQ ID NO 13
<211> LENGTH: 249
<212> TYPE: PRT
<213> ORGANISM: Artificial Sequence
<220> FEATURE:
<223> OTHER INFORMATION: h189-2 scFv

<400> SEQUENCE: 13

Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
        130                 135                 140

Lys Val Ser Cys Lys Ala Ser Gly Tyr Thr Phe Thr Ser Tyr Tyr Met
145                 150                 155                 160

His Trp Val Arg Gln Ala Pro Gly Gln Gly Leu Glu Trp Met Gly Trp
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
```

-continued

```
               210              215              220

Gly Gly Val Tyr Tyr Asp Leu Tyr Tyr Tyr Ala Leu Asp Tyr Trp Gly
225              230              235              240

Gln Gly Thr Leu Val Thr Val Ser Ser
                 245

<210> SEQ ID NO 14
<211> LENGTH: 108
<212> TYPE: PRT
<213> ORGANISM: Artificial Sequence
<220> FEATURE:
<223> OTHER INFORMATION: h189-3 VL

<400> SEQUENCE: 14

Asp Val Val Met Thr Gln Ser Pro Ala Phe Leu Ser Val Thr Pro Gly
1               5                10               15

Glu Lys Val Thr Ile Thr Cys Arg Ala Ser Gln Ser Ile Ser Asn Asn
                20               25               30

Leu His Trp Tyr Gln Gln Lys Pro Asp Gln Ala Pro Lys Leu Leu Ile
            35               40               45

Lys Ser Ala Ser Gln Ser Ile Ser Gly Val Pro Ser Arg Phe Ser Gly
        50               55               60

Ser Gly Ser Gly Thr Asp Phe Thr Phe Thr Ile Ser Ser Leu Glu Ala
65               70               75               80

Glu Asp Ala Ala Met Tyr Phe Cys Gln Gln Ser Asn Ser Trp Pro Tyr
                85               90               95

Thr Phe Gly Gln Gly Thr Lys Val Glu Ile Lys Arg
            100              105

<210> SEQ ID NO 15
<211> LENGTH: 123
<212> TYPE: PRT
<213> ORGANISM: Artificial Sequence
<220> FEATURE:
<223> OTHER INFORMATION: h189-3 VH

<400> SEQUENCE: 15

Gln Val Gln Leu Val Gln Ser Gly Ala Glu Val Lys Lys Pro Gly Ala
1               5                10               15

Ser Val Lys Val Ser Cys Lys Ala Ser Gly Tyr Thr Phe Thr Ser Tyr
                20               25               30

Trp Met His Trp Val Arg Gln Ala Pro Gly Gln Gly Leu Glu Trp Met
            35               40               45

Gly Lys Ile Asn Pro Ser Asn Gly Arg Thr Asn Tyr Ala Gln Lys Phe
        50               55               60

Gln Gly Arg Val Thr Met Thr Arg Asp Thr Ser Ile Ser Thr Ala Tyr
65               70               75               80

Met Glu Leu Ser Arg Leu Arg Ser Asp Asp Thr Ala Val Tyr Tyr Cys
                85               90               95

Ala Arg Gly Gly Val Tyr Tyr Asp Leu Tyr Tyr Tyr Ala Leu Asp Tyr
            100              105              110

Trp Gly Gln Gly Thr Leu Val Thr Val Ser Ser
        115              120

<210> SEQ ID NO 16
<211> LENGTH: 249
<212> TYPE: PRT
<213> ORGANISM: Artificial Sequence
<220> FEATURE:
```

<223> OTHER INFORMATION: h189-3 scFv

<400> SEQUENCE: 16

```
Asp Val Val Met Thr Gln Ser Pro Ala Phe Leu Ser Val Thr Pro Gly
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ala Pro Lys Leu Leu Ile
        35                  40                  45

Lys Ser Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Met Tyr Phe Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Trp Met
145                 150                 155                 160

His Trp Val Arg Gln Ala Pro Gly Gln Gly Leu Glu Trp Met Gly Lys
                165                 170                 175

Ile Asn Pro Ser Asn Gly Arg Thr Asn Tyr Ala Gln Lys Phe Gln Gly
            180                 185                 190

Arg Val Thr Met Thr Arg Asp Thr Ser Ile Ser Thr Ala Tyr Met Glu
            195                 200                 205

Leu Ser Arg Leu Arg Ser Asp Asp Thr Ala Val Tyr Tyr Cys Ala Arg
    210                 215                 220

Gly Gly Val Tyr Tyr Asp Leu Tyr Tyr Tyr Ala Leu Asp Tyr Trp Gly
225                 230                 235                 240

Gln Gly Thr Leu Val Thr Val Ser Ser
                245
```

<210> SEQ ID NO 17
<211> LENGTH: 108
<212> TYPE: PRT
<213> ORGANISM: Artificial Sequence
<220> FEATURE:
<223> OTHER INFORMATION: h189-4 VL

<400> SEQUENCE: 17

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Tyr
                85                  90                  95
```

Thr Phe Gly Gln Gly Thr Lys Val Glu Ile Lys Arg
            100                 105

<210> SEQ ID NO 18
<211> LENGTH: 123
<212> TYPE: PRT
<213> ORGANISM: Artificial Sequence
<220> FEATURE:
<223> OTHER INFORMATION: h189-4 VH

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Lys Ile Asn Pro Ser Asn Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Tyr Tyr Asp Leu Tyr Tyr Tyr Ala Leu Asp Tyr
            100                 105                 110

Trp Gly Gln Gly Thr Leu Val Thr Val Ser Ser
        115                 120

<210> SEQ ID NO 19
<211> LENGTH: 249
<212> TYPE: PRT
<213> ORGANISM: Artificial Sequence
<220> FEATURE:
<223> OTHER INFORMATION: h189-4 scFv

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
            35                  40                  45

Lys Ser Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Trp Met
145                 150                 155                 160

His Trp Val Arg Gln Ala Pro Gly Gln Gly Leu Glu Trp Met Gly Lys

```
                    165              170              175
Ile Asn Pro Ser Asn Gly Arg Thr Asn Tyr Ala Gln Lys Phe Gln Gly
              180              185              190

Arg Val Thr Met Thr Arg Asp Thr Ser Ile Ser Thr Ala Tyr Met Glu
          195              200              205

Leu Ser Arg Leu Arg Ser Asp Asp Thr Ala Val Tyr Tyr Cys Ala Arg
      210              215              220

Gly Gly Val Tyr Tyr Asp Leu Tyr Tyr Tyr Ala Leu Asp Tyr Trp Gly
  225              230              235              240

Gln Gly Thr Leu Val Thr Val Ser Ser
              245
```

```
<210> SEQ ID NO 20
<211> LENGTH: 747
<212> TYPE: DNA
<213> ORGANISM: Artificial Sequence
<220> FEATURE:
<223> OTHER INFORMATION: h189-1 scFv

<400> SEQUENCE: 20
gaaattgtgc tcactcaaag tcctgcaacc cttagcctgt ctccaggaga gcgagccact      60
ctgtcttgca gagccagcca atctatctct aataacctgc actggtatca acagaagcct     120
ggtcaggcac ctaggctcct gatatattcc gcgtctcagt ccatatcagg catccctgct     180
cgattcagcg gctctggtcc cggtactgat tttacgttga ctataagcag tcttgaacca     240
gaggattttg cagtttacta ttgtcagcag tcaaacagct ggccttatac cttcggccag     300
ggaaccaagg tagaaatcaa acgcggaagt acgtccggct caggaaagcc aggatctgga     360
gagggatcaa ctaagggaca agtgcagctg gtgcagtcag gagctgaagt taagaagcca     420
ggagcctccg tcaaggtctc ctgcaaggcc agcgggtata ctttcacgtc ctattatatg     480
cactgggtga ggcaagctcc tggtcaggga ttggagtgga tgggctggat caacccttca     540
aacggacgca ccaactacgc acagaaattc caaggtcggg taaccatgac gagagacacg     600
agtattagca cggcatatat ggagttgtct cgactgagga gcgacgacac ggccgtgtac     660
tattgcgcgc gaggtggggt gtactatgac ctgtattatt acgcattgga ctattggggg     720
cagggaacac tcgtcactgt ttccagc                                        747
```

```
<210> SEQ ID NO 21
<211> LENGTH: 747
<212> TYPE: DNA
<213> ORGANISM: Artificial Sequence
<220> FEATURE:
<223> OTHER INFORMATION: h189-2 scFv

<400> SEQUENCE: 21
gatgtcgtta tgacgcaaag cccagccttt ctctccgtaa cgcctggcga aaaagttacg      60
atcacctgcc gggcatctca aagtatcagt aacaatttgc attggtatca acagaaaccc     120
gaccaagccc caaaactcct tatcaagagc gctagtcaga gtatctccgg cgtcccttct     180
cgattctctg gctcaggtag tggaactgat ttcaccttca ctatatctag tttggaagct     240
gaagacgcgg ccacttacta ctgtcagcag tcaaatagtt ggccctacac cttcggtcaa     300
gggacaaaag tcgagatcaa acgaggctca acctctggta gcgggaagcc tggatctgga     360
gaaggcagca caaagggaca ggtgcagttg gtccaatctg ggcgggaggt taagaagcct     420
ggggcttctg ttaaagtgag ttgtaaggca tcaggttata ctttcacatc ctactacatg     480
```

-continued

```
cactgggttc ggcaggctcc gggccaggga cttgaatgga tggggtggat taatccaagc      540
aatggccgca ctaactatgc tcagaagttc aaggaaggg tcacaatgac tagagacact       600
tccatatcaa ccgcgtatat ggaactttca cgacttcgca gcgacgatac tgcggtctat      660 tattgtcgc gaggggggagt ttattatgac ctttactact acgcgcttga ttattgggga      720
cagggtaccc ttgttaccgt ttccagc                                           747
```

```
<210> SEQ ID NO 22
<211> LENGTH: 747
<212> TYPE: DNA
<213> ORGANISM: Artificial Sequence
<220> FEATURE:
<223> OTHER INFORMATION: h189-3 scFv

<400> SEQUENCE: 22
gatgtcgtta tgacgcaaag cccagccttt ctctccgtaa cgcctggcga aaaagttacg       60
atcacctgcc gggcatctca aagtatcagt aacaatttgc attggtatca acagaaaccc      120
gaccaagccc caaaactcct tatcaagagc gctagtcaga gtatctccgg cgtcccttct      180
cgattctctg gctcaggtag tggaactgat ttcaccttca ctatatctag tttggaagct      240
gaagacgcgg ccatgtactt ctgtcagcag tcaaatagtt ggccctacac cttcggtcaa      300
gggacaaaag tcgagatcaa acgaggctca acctctggta gcgggaagcc tggatctgga      360
gaaggcagca caaagggaca ggtgcagttg gtccaatctg gggcggaggt taagaagcct      420
ggggcttctg ttaaagtgag ttgtaaggca tcaggttata ctttcacatc ctactggatg      480
cactgggttc ggcaggctcc gggccaggga cttgaatgga tggggaaaat taatccaagc      540
aatggccgca ctaactatgc tcagaagttc aaggaaggg tcacaatgac tagagacact       600
tccatatcaa ccgcgtatat ggaactttca cgacttcgca gcgacgatac tgcggtctat      660 tattgtcgc gaggggggagt ttattatgac ctttactact acgcgcttga ttattgggga      720
cagggtaccc ttgttaccgt ttccagc                                           747
```

```
<210> SEQ ID NO 23
<211> LENGTH: 747
<212> TYPE: DNA
<213> ORGANISM: Artificial Sequence
<220> FEATURE:
<223> OTHER INFORMATION: h189-4 scFv

<400> SEQUENCE: 23
gaaatcgtgt tgacacagag ccctgcaacc ctttcacttt ccccaggcga acgcgcgacc       60
ctgtcatgcc gcgctagtca agtatatca aataacctcc actggtatca gcaaaagcct       120
ggtcaggccc cacgcttgtt gatcaaatct gcctctcaaa gcatcagtgg tattcccgct      180
agattctctg gtagcgggcc tgggaccgat ttcactttga ctatctcatc tttggaaccg      240
gaggatttcg ctgtctactt ttgccaacag agtaattcat ggccttatac gttcggacag      300
ggaacgaagg tagagattaa aagaggctct acaagcggtt ccggtaagcc gggctctggg      360
gaaggttcaa cgaaagggca agtacagctc gtacagtccg gggcagaagt taagaagccg      420
ggggcatccg tcaaagtatc atgtaaagcg agtggttata cgttcacaag ctactggatg      480
cattgggtac gccaagcccc aggccaagga ttggaatgga tgggtaagat taacccgagc      540
aatggaagga caaattacgc tcaaaagttc cagggacggg tcacaatgac gcgcgatacg      600
agcattagca cagcctacat ggagctttcc cgccttaggt cagatgacac tgctgtgtat      660
tattgcgcca gaggtggagt gtattacgac ctctattatt acgccctcga ctattgggga      720
```

-continued cagggtactc ttgttactgt gagtagc                                                    747

<210> SEQ ID NO 24
<211> LENGTH: 25
<212> TYPE: PRT
<213> ORGANISM: Artificial Sequence
<220> FEATURE:
<223> OTHER INFORMATION: CD8alpha transmembrane domain

<400> SEQUENCE: 24

Ile Tyr Ile Trp Ala Pro Leu Ala Gly Thr Cys Gly Val Leu Leu Leu
1               5                   10                  15

Ser Leu Val Ile Thr Leu Tyr Cys Lys
            20                  25

<210> SEQ ID NO 25
<211> LENGTH: 75
<212> TYPE: DNA
<213> ORGANISM: Artificial Sequence
<220> FEATURE:
<223> OTHER INFORMATION: CD8alpha transmembrane domain

<400> SEQUENCE: 25
atctacatct gggcgccctt ggccgggact tgtggggtcc ttctcctgtc actggttatc      60 acccttact gcaaa                                                          75

<210> SEQ ID NO 26
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 26

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 27
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 27
ttttgggtcc tcgtcgtagt tggaggggta cttgcctgtt atagcctcct ggttaccgta      60
gcatttatta tattctgggt g                                                  81

<210> SEQ ID NO 28
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 28

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

```
Pro Arg Asp Phe Ala Ala Tyr Arg Ser
        35                  40

<210> SEQ ID NO 29
<211> LENGTH: 123
<212> TYPE: DNA
<213> ORGANISM: Artificial Sequence
<220> FEATURE:
<223> OTHER INFORMATION: CD28 costimulatory domain

<400> SEQUENCE: 29
aggagtaaga ggagcaggct cctgcacagt gactacatga acatgactcc ccgccgcccc        60
gggcccaccc gcaagcatta ccagccctat gccccaccac gcgacttcgc agcctatcgc       120
tcc                                                                      123

<210> SEQ ID NO 30
<211> LENGTH: 40
<212> TYPE: PRT
<213> ORGANISM: Artificial Sequence
<220> FEATURE:
<223> OTHER INFORMATION: 4-1BB costimulatory domain

<400> SEQUENCE: 30

Arg Gly Arg Lys Lys Leu Leu Tyr Ile Phe Lys Gln Pro Phe Met Arg
1               5                   10                  15

Pro Val Gln Thr Thr Gln Glu Glu Asp Gly Cys Ser Cys Arg Phe Pro
            20                  25                  30

Glu Glu Glu Glu Gly Gly Cys Glu
        35                  40

<210> SEQ ID NO 31
<211> LENGTH: 120
<212> TYPE: DNA
<213> ORGANISM: Artificial Sequence
<220> FEATURE:
<223> OTHER INFORMATION: 4-1BB costimulatory domain

<400> SEQUENCE: 31
cggggcagaa agaaactcct gtatatattc aaacaaccat ttatgagacc agtacaaact        60
actcaagagg aagatggctg tagctgccga tttccagaag aagaagaagg aggatgtgaa       120

<210> SEQ ID NO 32
<211> LENGTH: 113
<212> TYPE: PRT
<213> ORGANISM: Artificial Sequence
<220> FEATURE:
<223> OTHER INFORMATION: CD3zeta signaling domain

<400> SEQUENCE: 32

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
            35                  40                  45

Lys Pro Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95
```

-continued

```
Ala Thr Lys Asp Thr Tyr Asp Ala Leu His Met Gln Ala Leu Pro Pro
            100                 105                 110

Arg

<210> SEQ ID NO 33
<211> LENGTH: 339
<212> TYPE: DNA
<213> ORGANISM: Artificial Sequence
<220> FEATURE:
<223> OTHER INFORMATION: CD3zeta signaling domain

<400> SEQUENCE: 33
ctgagagtga agttcagcag gagcgcagac gcccccgcgt accagcaggg ccagaaccag      60
ctctataacg agctcaatct aggacgaaga gaggagtacg atgttttgga caagagacgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaagggggca cgatggcctt taccagggtc tcagtacagc caccaaggac     300
acctacgacg cccttcacat gcaggccctg cccccctcgc                           339

<210> SEQ ID NO 34
<211> LENGTH: 114
<212> TYPE: PRT
<213> ORGANISM: Artificial Sequence
<220> FEATURE:
<223> OTHER INFORMATION: CD3zeta signaling domain

<400> SEQUENCE: 34

Leu Arg Val Lys Phe Ser Arg Ser Ala Asp Ala Pro Ala Tyr Gln Gln
1               5                   10                  15

Gly Gln Asn Gln Leu Phe Asn Glu Leu Asn Leu Gly Arg Arg Glu Glu
            20                  25                  30

Phe Asp Val Leu Asp Lys Arg Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Phe Gln Gly Leu Ser
                85                  90                  95

Thr Ala Thr Lys Asp Thr Phe Asp Ala Leu His Met Gln Ala Leu Pro
            100                 105                 110

Pro Arg

<210> SEQ ID NO 35
<211> LENGTH: 342
<212> TYPE: DNA
<213> ORGANISM: Artificial Sequence
<220> FEATURE:
<223> OTHER INFORMATION: CD3zeta signaling domain

<400> SEQUENCE: 35
ctgagagtga agttcagcag gagcgcagac gcccccgcgt accagcaggg ccagaaccag      60
ctctttaacg agctcaatct aggacgaaga gaggagttcg atgttttgga caagagacgt     120
ggccgggacc ctgagatggg gggaaagccg cagagaagga agaaccctca ggaaggcctg     180
tacaatgaac tgcagaaaga taagatggcg gaggcctaca gtgagattgg gatgaaaggc     240
```

-continued gagcgccgga ggggcaaggg gcacgatggc cttttccagg gtctcagtac agccaccaag    300
gacacctttg acgcccttca catgcaggcc ctgccccctc gc    342

<210> SEQ ID NO 36
<211> LENGTH: 20
<212> TYPE: PRT
<213> ORGANISM: Artificial Sequence
<220> FEATURE:
<223> OTHER INFORMATION: B2M signal peptide

<400> SEQUENCE: 36

Met Ser Arg Ser Val Ala Leu Ala Val Leu Ala Leu Leu Ser Leu Ser
1               5                   10                  15

Gly Leu Glu Ala
            20

<210> SEQ ID NO 37
<211> LENGTH: 60
<212> TYPE: DNA
<213> ORGANISM: Artificial Sequence
<220> FEATURE:
<223> OTHER INFORMATION: B2M signal peptide

<400> SEQUENCE: 37
atgtcccgct ctgttgcttt ggctgtgctg gccctttttgt cccttagcgg actggaggcc    60

<210> SEQ ID NO 38
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 38

Met Ala Leu Pro Val Thr Ala Leu Leu Leu Pro Leu Ala Leu Leu Leu
1               5                   10                  15

His Ala Ala Arg Pro
            20

<210> SEQ ID NO 39
<211> LENGTH: 63
<212> TYPE: DNA
<213> ORGANISM: Artificial Sequence
<220> FEATURE:
<223> OTHER INFORMATION: CD8alpha signal peptide

<400> SEQUENCE: 39
atggccttac cagtgaccgc cttgctcctg ccgctggcct tgctgctcca cgccgccagg    60
ccg    63

<210> SEQ ID NO 40
<211> LENGTH: 45
<212> TYPE: PRT
<213> ORGANISM: Artificial Sequence
<220> FEATURE:
<223> OTHER INFORMATION: CD8alpha hinge region

<400> SEQUENCE: 40

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp

-continued

```
              35               40               45

<210> SEQ ID NO 41
<211> LENGTH: 135
<212> TYPE: DNA
<213> ORGANISM: Artificial Sequence
<220> FEATURE:
<223> OTHER INFORMATION: CD8alpha hinge region

<400> SEQUENCE: 41
accacgacgc cagcgccgcg accaccaaca ccggcgccca ccatcgcgtc gcagcccctg     60
tccctgcgcc cagaggcgtg ccggccagcg gcgggggggcg cagtgcacac gagggggctg    120
gacttcgcct gtgat                                                     135

<210> SEQ ID NO 42
<211> LENGTH: 39
<212> TYPE: PRT
<213> ORGANISM: Artificial Sequence
<220> FEATURE:
<223> OTHER INFORMATION: CD28 hinge region

<400> SEQUENCE: 42

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 43
<211> LENGTH: 117
<212> TYPE: DNA
<213> ORGANISM: Artificial Sequence
<220> FEATURE:
<223> OTHER INFORMATION: CD28 hinge region

<400> SEQUENCE: 43
attgaagtta tgtatcctcc tccttaccta gacaatgaga agagcaatgg aaccattatc     60
catgtgaaag ggaaacacct ttgtccaagt cccctatttc ccggaccttc taagccc        117

<210> SEQ ID NO 44
<211> LENGTH: 12
<212> TYPE: PRT
<213> ORGANISM: Artificial Sequence
<220> FEATURE:
<223> OTHER INFORMATION: IgG4 hinge region

<400> SEQUENCE: 44

Glu Ser Lys Tyr Gly Pro Pro Cys Pro Pro Cys Pro
1               5                   10

<210> SEQ ID NO 45
<211> LENGTH: 36
<212> TYPE: DNA
<213> ORGANISM: Artificial Sequence
<220> FEATURE:
<223> OTHER INFORMATION: IgG4 hinge region

<400> SEQUENCE: 45
gaaagcaaat acgggccgcc gtgtccaccc tgtccg                               36
```

CD7-TARGETING HUMANIZED ANTIBODY AND USE THEREOF

RELATED APPLICATIONS

This application is a United States National Stage Application filed under 35 U.S.C § 371 of PCT Patent Application Serial No. PCT/CN2021/127570, filed Oct. 29, 2021, which claims priority to Chinese Patent Application Serial No. CN 202011208669.1, filed Nov. 3, 2020, the disclosure of all of which are hereby incorporated by reference in their entirety.

TECHNICAL FIELD

The present disclosure belongs to the field of immunotherapy. More specifically, the present disclosure relates to a CD7-targeting humanized antibody and use thereof in the prevention and/or treatment and/or diagnosis of diseases.

BACKGROUND ART

CD7 is a cell surface glycoprotein with a molecular weight of about 40 kDa and belongs to the immunoglobulin superfamily CD7 is expressed in most T cells, NK cells, myeloid cells, T cell acute lymphoblastic leukemia/lymphoma, acute myelogenous leukemia and chronic myelogenous leukemia. It has been reported that the CD7 molecule acts as a co-stimulatory signal during T cell activation through the binding with its ligand K12/SECTM1. In addition, disruption of the CD7 molecule in mouse T progenitor cells has been reported to still result in normal T cell development and homeostasis, suggesting that CD7 does not appear to have critical effects on T cell development and function, making it a very suitable therapeutic target for the treatment of T-cell acute lymphoblastic leukemia (T-ALL). Indeed, CD7 has been extensively studied as a target of cytotoxic molecules for the treatment of leukemia and lymphoma.

The present disclosure aims to provide a CD7-targeting humanized antibody and use thereof in the prevention and/or treatment and/or diagnosis of diseases.

SUMMARY

In a first aspect, the present disclosure provides a CD7-targeting humanized antibody comprising a light chain variable region and a heavy chain variable region, wherein the light chain variable region comprises CDR-L1 as set forth in SEQ ID NO: 1, CDR-L2 as set forth in SEQ ID NO: 2 and CDR-L3 as set forth in SEQ ID NO: 3, the heavy chain variable region comprises CDR-H1 as set forth in SEQ ID NO: 4, CDR-H2 as set forth in SEQ ID NO: 5 and CDR-H3 as set forth in SEQ ID NO: 6, and the light chain variable region has at least 90% sequence identity to an amino acid sequence selected from the group consisting of SEQ ID NOs: 8, 11, 14 and 17, and the heavy chain variable region has at least 90% sequence identity to an amino acid sequence selected from the group consisting of SEQ ID NOs: 9, 12, 15 and 18.

In an embodiment, the anti-CD7 humanized antibody comprises a light chain variable region selected from the group consisting of SEQ ID NOs: 8, 11, 14 and 17 and a heavy chain variable region selected from the group consisting of 9, 12, 15 and 18.

In an embodiment, the anti-CD7 humanized antibody has an amino acid sequence selected from the group consisting of SEQ ID NOs: 10, 13, 16 and 19.

The present disclosure further provides a nucleic acid molecule encoding the anti-CD7 humanized antibody as described above. Therefore, in an embodiment, the nucleic acid molecule encoding the anti-CD7 humanized antibody has at least 90%, at least 91%, at least 92%, at least 93%, at least 94%, at least 95%, at least 96%, at least 97%, at least 98%, at least 99% or 100% sequence identity to a nucleotide sequence selected from the group consisting of SEQ ID NOs: 20-23, and the encoded anti-CD7 humanized antibody specifically binds to CD7 antigen. Preferably, the nucleic acid molecule encoding the anti-CD7 humanized antibody is selected from SEQ ID NOs: 20-23.

In another aspect, the present disclosure further provides a multispecific antibody (preferably bispecific antibody or trispecific antibody), comprising the anti-CD7 humanized antibody as described above, and one or more second antibodies or antigen-binding portions thereof that specifically bind to antigens different from CD7.

In an embodiment, the second antibody or antigen-binding portion thereof may be in the form of any antibody or antibody fragment, such as a full-length antibody, Fab, Fab', (Fab')$_2$, Fv, scFv, scFv-scFv, a minibody, a diabody or sdAb.

The present disclosure further provides a vector comprising a nucleic acid molecule encoding the anti-CD7 humanized antibody or the multispecific antibody as described above, and a host cell expressing the anti-CD7 humanized antibody or the multispecific antibody.

In another aspect, the present disclosure further provides a chimeric antigen receptor, comprising the anti-CD7 humanized antibody of the present disclosure, a transmembrane domain and an intracellular signaling domain. Preferably, the chimeric antigen receptor further comprises one or more co-stimulatory domains. More preferably, the chimeric antigen receptor comprises the anti-CD7 humanized antibody or the multispecific antibody comprising the anti-CD7 humanized antibody as provided herein, a CD8a transmembrane region, a CD28 or 4-1BB co-stimulatory domain, and a CD3 intracellular signaling domain.

The present disclosure further provides a nucleic acid molecule encoding the CD7-targeting chimeric antigen receptor as defined above, and a vector comprising the nucleic acid molecule.

The present disclosure further provides a cell, preferably an immune cell, such as a T cell, a NK cell, a NKT cell, a macrophage, and a dendritic cell, comprising the CD7-targeting chimeric antigen receptor as defined above.

In another aspect, the present disclosure further provides an antibody conjugate comprising the anti-CD7 humanized antibody defined in the present disclosure and a second functional structure, wherein the second functional structure is selected from the group consisting of Fc, a radioisotope, a structure moiety for extending half-life, a detectable marker and a drug.

In an embodiment, the structure moiety for extending half-life is selected from the group consisting of an albumin-binding structure, a transferrin-binding structure, a polyethylene glycol molecule, a recombinant polyethylene glycol molecule, human serum albumin, a fragment of human serum albumin, and a polypeptide (including an antibody) binding to human serum albumin. In an embodiment, the detectable marker is selected from the group consisting of a fluorophore, a chemiluminescent compound, a bioluminescent compound, an enzyme, an antibiotic resistance gene, and a contrast agent. In an embodiment, and the drug is selected from the group consisting of a cytotoxin and an immunomodulator.

In another aspect, the present disclosure further provides a detection kit comprising the humanized antibody, the multispecific antibody, the antibody conjugate or the chimeric antigen receptor described in the present disclosure.

In another aspect, the present disclosure further provides a pharmaceutical composition comprising the humanized antibody, the chimeric antigen receptor, the multispecific antibody or the antibody conjugate described in the present disclosure, and one or more pharmaceutically acceptable excipients.

In another aspect, the present disclosure further provides a method for treating and/or preventing and/or diagnosing diseases associated with CD7 expression, comprising administering to a subject the humanized antibody, the chimeric antigen receptor, the multispecific antibody, the antibody conjugate or the pharmaceutical composition as described above.

DETAILED DESCRIPTION OF EMBODIMENTS

Unless otherwise specified, all scientific and technical terms used herein have the same meaning as commonly understood by one of ordinary skill in the art to which this disclosure belongs.

Anti-CD7 Humanized Antibody

As used herein, the term "antibody" has the broadest meaning understood by those skilled in the art and includes monoclonal antibodies (including whole antibodies), polyclonal antibodies, multivalent antibodies, multispecific antibodies (e.g., bispecific antibodies), and antibody fragments or synthetic polypeptides carrying one or more CDR sequences capable of exhibiting the desired biological activity. The antibodies of the disclosure may be of any class (e.g., IgG, IgE, IgM, IgD, IgA, etc.) or subclass (e.g., IgG1, IgG2, IgG2a, IgG3, IgG4, IgA1, IgA2, etc.).

Typically, whole antibodies comprise two heavy chains and two light chains disulfide-bonded together, each light chain being disulfide-bonded to a respective heavy chain, to form a "Y" configuration. Each heavy chain comprises a heavy chain variable region (VH) and a heavy chain constant region, wherein the heavy chain variable region contains three complementarity determining regions (CDRs): CDR-H1, CDR-H2 and CDR-H3, and the heavy chain constant region contains three constant domains: CH1, CH2 and CH3. Each light chain comprises a light chain variable region (VL) and a light chain constant region, wherein the light chain variable region contains three CDRs: CDR-L1, CDR-L2 and CDR-L3, and the light chain constant region contains a constant domain CL. In the heavy/light chain variable regions, the CDRs are separated by more conserved framework regions (FRs). The heavy/light chain variable regions are responsible for the recognition and binding of the antigen, while the constant regions can mediate the binding of the antibody to host tissues or factors, including various cells of the immune system (e.g., effector cells) and the first component of the classical complement system.

The precise amino acid sequence boundaries for a given CDR or FR can be readily determined using a number of numbering schemes well known in the art, including: Kabat et al. (1991), "Sequences of Proteins of Immunological Interest," 5th Edition, Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol 262:732-745 (1996), "Antibody-antigen interactions: Contact analysis and binding sitetopography," J. Mol. Biol. 262, 732-745" ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70 ("Aho" numbering scheme); and Martin et al., "Modeling antibody hypervariable loops: a combined algorithm," PNAS, 1989, 86(23): 9268-9272 ("AbM" numbering scheme).

The boundaries of a given CDR or FR may vary depending on the scheme used for identification. For example, the Kabat scheme is based on structural alignments, while the Chothia scheme is based on structural information. Both the Kabat and Chothia numbering schemes are based on the sequence lengths of the most common antibody regions where insertions are provided by caret letters (e.g., "30a") and deletions occur in some antibodies. These two schemes place certain insertions and deletions ("indels") at different positions, resulting in different numbering. The Contact scheme is based on the analysis of complex crystal structures and is similar in many respects to the Chothia numbering scheme. The AbM scheme is a compromise between the Kabat and Chothia definitions and is based on the scheme used by the AbM antibody modeling software of Oxford Molecular.

Thus, unless otherwise specified, a "CDR" of a given antibody or region thereof (e.g., variable region thereof) is understood to encompass the CDRs defined by any of the above schemes or other known schemes. For example, where it is specified that a particular CDR (e.g., CDR3) contains a given amino acid sequence, it is understood that such a CDR may also have the sequence of the corresponding CDR (e.g., CDR3) as defined by any of the above schemes or other known schemes. Likewise, unless otherwise specified, FRs for a given antibody or region thereof (e.g., variable region thereof) are understood to encompass FRs as defined by any of the above schemes or other known schemes.

As used herein, a "humanized" antibody refers to an antibody in which all or substantially all CDR amino acid residues are derived from non-human CDRs and all or substantially all FR amino acid residues are derived from human FRs. "Humanized forms" of a non-human antibody refer to variants of such non-human antibody that have been humanized to generally reduce immunogenicity in humans, while retaining the specificity and affinity of the parent non-human antibody. In some embodiments, some FR residues in a humanized antibody are substituted with corresponding residues from a non-human antibody (e.g., an antibody from which the CDR residues are derived), e.g., to restore or improve antibody specificity or affinity.

Humanized antibodies and methods for their preparation are well known to those skilled in the art, see e.g., Almagro and Fransson, Front. Biosci. 13:1619-1633 (2008). Human framework regions that can be used for humanization include, but are not limited to: framework regions selected using a "best fit" approach; framework regions derived from the consensus sequences of human antibodies of a particular subgroup of light or heavy chain variable regions; human mature (somatically mutated) framework regions or human germline framework regions; and framework regions obtained from screening FR libraries.

As used herein, the term "antibody fragment" or "antigen-binding portion" comprises only a portion of an intact antibody, and typically comprises the antigen-binding site of the intact antibody and thus retains the ability to bind antigen. Examples of antibody fragments in the present disclosure include, but are not limited to: Fab, Fab', F(ab')2, Fd fragment, Fd', Fv fragment, scFv, disulfide-linked Fv (sdFv), antibody heavy chain variable region (VH) or light chain variable region (VL), linear antibody, "diabody" with two antigen binding sites, single domain antibody, nanobody, a natural ligand for the antigen or a functional fragment thereof. Accordingly, an "antibody" of the present disclosure encompasses antibody fragments as defined above.

In an embodiment, the anti-CD7 humanized antibody of the disclosure is a scFv. "Single-chain antibody" and "scFv" are used interchangeably herein and refer to an antibody formed by linking the heavy chain variable region (VH) and the light chain variable region (VL) of an antibody through a linker. The optimal length and/or amino acid composition of the linker can be selected. The length of the linker can significantly affect the folding and interaction of the variable domain of scFv. In fact, if shorter linkers (e.g., with between 5-10 amino acids) are used, intrachain folding can be prevented. For selection of linker size and composition, see, e.g., Hollinger et al., 1993 Proc Natl Acad. Sci. U.S.A. 90:6444-6448; U.S. Patent Application Publication Nos. 2005/0100543, 2005/0175606, 2007/0014794 and PCT Publication Nos. WO2006/020258 and WO2007/024715, the entire contents of which are incorporated herein by reference. A scFv may comprise VH and VL linked in any order, e.g. VH-linker-VL or VL-linker-VH.

In some embodiments, the present disclosure provides an anti-CD7 humanized antibody comprising a light chain variable region and a heavy chain variable region, wherein the light chain variable region comprises CDR-L1 as set forth in SEQ ID NO: 1, CDR-L2 as set forth in SEQ ID NO: 2 and CDR-L3 as set forth in SEQ ID NO: 3, the heavy chain variable region comprises CDR-H1 as set forth in SEQ ID NO: 4, CDR-H2 as set forth in SEQ ID NO: 5 and CDR-H3 as set forth in SEQ ID NO: 6, and the light chain variable region has at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 8, 11, 14 and 17, and the heavy chain variable region has at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 9, 12, 15 and 18.

In an embodiment, the anti-CD7 humanized antibody comprises a light chain variable region selected from the group consisting of SEQ ID NOs: 8, 11, 14 and 17 and a heavy chain variable region selected from the group consisting of 9, 12, 15 and 18.

In an embodiment, the anti-CD7 humanized antibody has an amino acid sequence selected from the group consisting of SEQ ID NOs: 10, 13, 16 and 19.

As used herein, the term "sequence identity" means the degree to which two (nucleotide or amino acid) sequences in alignment have the same residue at the same position, and is usually expressed as a percentage. Preferably, identity is determined over the entire length of the sequences being compared. Therefore, two copies of the exact same sequence have 100% identity. Those skilled in the art know that several algorithms can be used to determine sequence identity, such as Blast (Altschul et al. (1997) Nucleic Acids Res. 25:3389-3402), Blast2 (Altschul et al. (1990) J. Mol. Biol. 215: 403-410), Smith-Waterman (Smith et al. (1981) J. Mol. Biol. 147:195-197) and Clustal W.

In an aspect, the present disclosure further provides a multispecific antibody (preferably a bispecific antibody or a trispecific antibody) comprising the anti-CD7 humanized antibody as described above, and one or more second antibodies that specifically bind to antigens different from CD7.

As used herein, the term "multispecific" means that the antigen binding protein has polyepitopic specificity (i.e., is capable of specifically binding two, three or more different epitopes on one biomolecule or is capable of specifically binding epitopes on two, three or more different biomolecules). As used herein, the term "bispecific" means that an antigen binding protein has two different antigen binding specificities.

In an embodiment, the second antibody may be in the form of any antibody or antibody fragment, such as a full-length antibody, Fab, Fab', (Fab') 2, Fv, scFv, scFv-scFv, a minibody, a diabody or sdAb.

Thus, in an embodiment, the second antibody targets an antigen selected from the group consisting of: BCMA, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, angiogenic factor, VEGF, PIGF, ED-B fibronectin, oncogene, oncogene product, CD66a-d, necrosis antigen, Ii, IL-2, T101, TAC, IL-6, ROR1, TRAIL-R1 (DR4), TRAIL-R2 (DR5), tEGFR, Her2, L1-CAM, mesothelin, CEA, hepatitis B surface antigen, antifolate receptor, CD24, CD30, CD44, EGFR, EGP-2, EGP-4, EPHa2, ErbB2, ErbB3, ErbB4, ErbB dimer, EGFR vIII, FBP, FCRL5, FCRH5, fetal acetylcholine receptor, GD2, GD3, G protein-coupled receptor type C family 5D (GPRC5D), HMW-MAA, IL-22R-α, IL-13R-α2, kdr, κ light chain, Lewis Y, L1-cell adhesion molecule (L1-CAM), melanoma-associated antigen (MAGE)-A1, MAGE-A3, MAGE-A6, melanoma preferentially expressed antigen (PRAME), survivin, EGP2, EGP40, TAG72, B7-H6, IL-13 receptor a2 (IL-13Ra2), CA9, CD171, G250/CAIX, HLA-A1, HLA-A2, NY-ESO-1, PSCA, folate receptor-a, CD44v6, CD44v7/8, avb6 integrin, 8H9, NCAM, VEGF receptor, 5T4, fetal AchR, NKG2D ligand, dual antigens, antigens associated with common tags, cancer-testis antigen, MUC1, MUC16, NY-ESO-1, MART-1, gp100, carcinoembryonic antigen, VEGF-R2, carcinoembryonic antigen (CEA), prostate specific antigen, PSMA, Her2/neu, estrogen receptor, progesterone receptor, ephrin B2, CD123, c-Met, GD-2, O-acetylated GD2 (OGD2), CE7, Wilms tumor 1 (WT-1), cyclin, cyclin A2, CCL-1, hTERT, MDM2, CYP1B, WT1, survivin, AFP, p53, cyclin (D1), CS-1, BAFF-R, TACI, CD56, TIM-3, CD123, L1-cell adhesion molecules, MAGE-A1, MAGEA3, cell cyclins (e.g., cyclin A1 (CCNA1)) and/or pathogen-specific antigens, biotinylated molecules, molecules expressed by HIV, HCV, HBV and/or other pathogens; and/or neo-epitopes or neoantigens.

Nucleic Acid, Vector, Host Cell

In another aspect, the present disclosure relates to a nucleic acid molecule encoding the anti-CD7 humanized antibody or multispecific antibody of the present disclosure. The nucleic acid of the present disclosure may be RNA, DNA or cDNA. According to an embodiment of the present disclosure, the nucleic acid of the present disclosure is a substantially isolated nucleic acid.

In an embodiment, the nucleic acid molecule encoding the anti-CD7 humanized antibody has at least 90%, at least 91%, at least 92%, at least 93%, at least 94%, at least 95%, at least 96%, at least 97%, at least 98%, at least 99% or 100% sequence identity to a nucleotide sequence selected from the group consisting of SEQ ID NOs: 20-23, and the encoded anti-CD7 humanized antibody specifically binds to CD7 antigen. Preferably, the nucleic acid molecule encoding the anti-CD7 humanized antibody is set forth in SEQ ID NOs:

The nucleic acid of the present disclosure may also be in the form of, may be present in and/or may be part of a vector, such as a plasmid, cosmid or YAC. The vector may especially be an expression vector, i.e., a vector providing for expression of the anti-CD7 humanized antibody in vitro and/or in vivo (i.e., in a suitable host cell, host organism and/or expression system). The expression vector typically comprises at least one nucleic acid molecule of the present disclosure operably linked to one or more suitable expression regulatory elements (e.g., promoter, enhancer, terminator, etc.). Selection of such regulatory elements and their sequences for expression in a particular host is well known to those skilled in the art. Specific examples of regulatory elements and other elements useful or necessary for expression of the CD7 humanized antibodies of the present disclosure include, but are not limited to, promoter, enhancer, terminator, integrator, selectable marker, leader sequence, reporter gene.

In another aspect, the present disclosure further provides a host cell expressing the anti-CD7 humanized antibody, the multispecific antibody of the present disclosure and/or a host cell containing the nucleic acid or vector of the present disclosure. Preferred host cells of the present disclosure are bacterial cells, fungal cells or mammalian cells.

Suitable bacterial cells include cells of Gram-negative bacterial strains (e.g., *Escherichia coli* strains, *Proteus* strains, and *Pseudomonas* strains) and Gram-positive bacterial strains (e.g., *Bacillus* strains, *Streptomyces* strains, *Staphylococcus* strains and *Lactococcus* strains).

Suitable fungal cells include cells of species of *Trichoderma, Neurospora*, and *Aspergillus*; or cells of species of *Saccharomyces* (e.g., *Saccharomyces cerevisiae*), *Schizosaccharomyces* (e.g., *Schizosaccharomyces pombe*), *Pichia* (e.g., *Pichia pastoris* and *Pichia methanolica*) and *Hansenula*.

Suitable mammalian cells include, for example, HEK293 cells, CHO cells, BHK cells, HeLa cells, COS cells, and the like.

However, amphibian cells, insect cells, plant cells, and any other cells known in the art for expressing heterologous proteins can also be used in the present disclosure.
Chimeric Antigen Receptor In another aspect, the present disclosure further provides a recombinant receptor, such as a recombinant TCR receptor or a chimeric antigen receptor comprising the anti-CD7 humanized antibody as described above. Preferably, the present disclosure further provides a chimeric antigen receptor comprising the anti-CD7 humanized antibody as described above.

As used herein, the term "chimeric antigen receptor" or "CAR" refers to an artificially constructed hybrid polypeptide that generally includes a ligand-binding domain (e.g., an antigen-binding portion of an antibody), a transmembrane domain, an optional co-stimulatory domain, and an intracellular signaling domain, which domains being connected by linkers. CARs are able to redirect the specificity and reactivity of T cells and other immune cells to a selected target in a non-MHC-restricted manner through the antigen-binding properties of antibodies.

In an embodiment, the present disclosure provides a chimeric antigen receptor comprising the anti-CD7 humanized antibody or the multispecific antibody comprising the anti-CD7 humanized antibody, a transmembrane domain and an intracellular signaling domain.

As used herein, the term "transmembrane domain" refers to a polypeptide structure that enables expression of a chimeric antigen receptor on the surface of an immune cell (e.g., a lymphocyte, an NK cell, or an NKT cell), and guides a cellular response of the immune cell against the target cell. The transmembrane domain may be natural or synthetic, and also may be derived from any membrane-bound protein or transmembrane protein. The transmembrane domain is capable of signaling when the chimeric antigen receptor binds to the target antigen. The transmembrane domains particularly suitable for use in the present disclosure may be derived from, for example, a TCRα chain, a TCRβ chain, a TCRγ chain, a TCRδ chain, a CD3ζ subunit, a CD3ε subunit, a CD3γ subunit, a CD3δ subunit, CD45, CD4, CD5, CD8α, CD9, CD16, CD22, CD33, CD28, CD37, CD64, CD80, CD86, CD134, CD137, CD154, and functional fragments thereof. Alternatively, the transmembrane domain may be synthesized and may mainly contain hydrophobic residues such as leucine and valine. Preferably, the transmembrane domain is derived from CD8a chain or CD28, and has at least 70%, preferably at least 80%, more preferably at least 90%, at least 95%, at least 97% or at least 99% or 100% sequence identity to an amino acid sequence as set forth in SEQ ID NO: 24 or 26, or the encoding sequence thereof has at least 70%, preferably at least 80%, more preferably at least 90%, at least 95%, at least 97% or at least 99% or 100% sequence identity to a nucleic acid molecule as set forth in SEQ ID NO: 25 or 27.

As used herein, the term "intracellular signaling domain" refers to a protein portion that transduces an effector function signal and guides a cell to perform a specified function. In an embodiment, the intracellular signaling domain contained in the chimeric antigen receptor of the present disclosure may be intracellular sequences of a T cell receptor and a co-receptor, upon binding of antigen receptor, which act together to initiate signaling, as well as any derivative or variant of these sequences and any synthetic sequence having the same or similar function. The intracellular signaling domain may contain many immunoreceptor tyrosine-based activation motifs (ITAM). Non-limiting examples of intracellular signaling domain of the present disclosure include, but are not limited to, intracellular regions of FcRγ, FcRβ, CD3γ, CD3δ, CD3ε, CD3ζ; CD22, CD79a, CD79b, and CD66d. In a preferred embodiment, the signaling domain of the CAR of the present disclosure may contain a CD3ζ intracellular region, which has at least 70%, preferably at least 80%, more preferably at least 90%, at least 95%, at least 97%, or at least 99% or 100% sequence identity to an amino acid sequence as set forth in SEQ ID NO: 32 or 34, or the encoding sequence thereof has at least 70%, preferably at least 80%, more preferably at least 90%, at least 95%, at least 97%, or at least 99% or 100% sequence identity to a nucleic acid molecule as set forth in 33 or 35.

In an embodiment, the chimeric antigen receptors of the present disclosure may further comprise a hinge region located between the antibody and the transmembrane domain. As used herein, the term "hinge region" generally refers to any oligopeptide or polypeptide that functions to link a transmembrane domain to an antibody. Specifically, the hinge region serves to provide greater flexibility and accessibility to the antibody. The hinge region may comprise up to 300 amino acids, preferably 10 to 100 amino acids and most preferably 25 to amino acids. The hinge region may be completely or partially derived from a natural molecule, for example, completely or partially from the extracellular region of CD8, CD4 or CD28, or completely or partially from an antibody constant region. Alternatively, the hinge region may be a synthetic sequence corresponding to a naturally occurring hinge sequence, or may be a completely synthetic hinge sequence. In a preferred embodiment, the hinge region comprises a hinge region portion of CD8α, CD28, an Fc γ RIII α receptor, IgG4, or IgG1, more preferably a hinge from CD8α, CD28 or IgG4, and has at least 70%, preferably at least 80%, more preferably at least 90%, at least 95%, at least 97% or at least 99% or 100% sequence identity to an amino acid sequence as set forth in SEQ ID NO: 40, 42 or 44, or the encoding sequence thereof has at least 70%, preferably at least 80%, more preferably at least 90%, at least 95%, at least 97% or at least 99% or 100% sequence identity to a nucleic acid molecule as set forth in SEQ ID NO: 41, 43 or 45.

In an embodiment, the chimeric antigen receptor may also comprise one or more co-stimulatory domains. The co-stimulatory domain may be an intracellular functional signaling domain from a co-stimulatory molecule, which comprises the entire intracellular portion of the co-stimulatory molecule, or a functional fragment thereof. A "costimulatory molecule" refers to a cognate binding partner that specifically binds to a costimulatory ligand on a T cell, thereby mediating a costimulatory response (e.g., proliferation) of the T cell. Costimulatory molecules include, but are not limited to, MHC class 1 molecules, BTLA, and Toll ligand receptors. Non-limiting examples of costimulatory domains of the present disclosure include, but are not limited to, costimulatory signaling domains derived from the following proteins: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, LAT, NKG2C, SLP76, PD-1, LIGHT, TRIM, and ZAP70. Preferably, the costimulatory domain of the CAR of the present disclosure is from 4-1BB, CD28 or 4-1BB+CD28. In an embodiment, the 4-1BB co-stimulatory domain has at least 70%, preferably at least 80%, more preferably at least 90%, at least 95%, at least 97% or at least 99% or 100% sequence identity to an amino acid sequence as set forth in SEQ ID NO: 30, or the coding sequence thereof has at least 70%, preferably at least 80%, more preferably at least 90%, at least 95%, at least 97% or at least 99% or 100% sequence identity to the nucleic acid molecule as set forth in SEQ ID NO: 31. In an embodiment, the CD28 co-stimulatory domain has at least 70%, preferably at least 80%, more preferably at least 90%, at least 95%, at least 97% or at least 99% or 100% sequence identity to an amino acid sequence as set forth in SEQ ID NO: 28, or the coding sequence thereof has at least 70%, preferably at least 80%, more preferably at least 90%, at least 95%, at least 97% or at least 99% or 100% sequence identity to the nucleic acid molecule as set forth in SEQ ID NO: 29.

In an embodiment, the CAR of the present disclosure may further comprise a signal peptide such that when it is expressed in a cell such as a T cell, the nascent protein is directed to the endoplasmic reticulum and subsequently to the cell surface. The core of the signal peptide may contain a long hydrophobic amino acid segment, which has a tendency to form a single α-helix. At the end of the signal peptide, there is usually an amino acid segment capable of being recognized and cleaved by signal peptidase. The signal peptidase can cleave during or after translocation, so as to generate free signal peptide and mature protein. Then, the free signal peptide is digested by a specific protease.

Signal peptides that can be used in the present disclosure are well known to those skilled in the art, for example, signal peptides derived from B2M, CD8α, IgG1, GM-CSFRα, and the like. In an embodiment, the signal peptide that can be used in the present disclosure is from B2M or CD8α, and has at least 70%, preferably at least 80%, more preferably at least 90%, at least 95%, at least 97% or at least 99% or 100% sequence identity to an amino acid sequence as set forth in SEQ ID NO: 103 or SEQ ID NO: 36 or 38, or the coding sequence thereof has at least 70%, preferably at least 80%, more preferably at least 90%, at least 95%, at least 97% or at least 99% or 100% sequence identity to the nucleic acid molecule as set forth in SEQ ID NO: 37 or 39.

In an embodiment, the CAR comprises the anti-CD7 humanized antibody or the multispecific antibody comprising the anti-CD7 humanized antibody as provided herein, a CD8α transmembrane region, a CD28 or 4-1BB co-stimulatory domain, and a CD3ζ intracellular signaling domain. In this embodiment, the CAR may further comprise a signal peptide from B2M, CD8a, IgG1 or GM-CSFRα.

The present disclosure further provides a nucleic acid molecule encoding the CD7-targeting chimeric antigen receptor as defined above, and a vector comprising the nucleic acid molecule.

As used herein, the term "vector" is an intermediary nucleic acid molecule used to transfer (exogenous) genetic material into a host cell, and in the host cell the nucleic acid molecule can be, for example, replicated and/or expressed. The vector generally includes targeting vectors and expression vectors. The "targeting vector" is a medium that delivers an isolated nucleic acid to the interior of a cell by, for example, homologous recombination or by using a hybrid recombinase of a sequence at specific target site. The "expression vector" is a vector used for transcription of heterologous nucleic acid sequences (for example, those sequences encoding the chimeric antigen receptor polypeptides of the present disclosure) in suitable host cells and the translation of their mRNAs. Suitable vectors that can be used in the present disclosure are known in the art, and many are commercially available. In an embodiment, the vector of the present disclosure includes, but is not limited to, plasmid, virus (e.g., retrovirus, lentivirus, adenovirus, vaccinia virus, Rous sarcoma virus (RSV), polyoma virus, and adeno-associated virus (AAV), etc.), phage, phagemid, cosmid, and artificial chromosome (including BAC and YAC). The vector itself is usually a nucleic acid molecule, and usually is a DNA sequence containing an insert (transgene) and a larger sequence as "backbone" of the vector. Engineered vector typically also contains an origin autonomously replicating in the host cell (if stable expression of polynucleotide is desired), a selectable marker, and a restriction enzyme cleavage site (e.g., a multiple cloning site, MCS). The vectors may additionally contain elements such as a promoter, a poly-A tail (polyA), 3' UTR, an enhancer, a terminator, an insulator, an operon, a selectable marker, a reporter gene, a targeting sequence, and/or a protein purification tag. In a specific embodiment, the vector is an in vitro transcription vector.

Engineered Immune Cells

In an aspect, the present disclosure further provides an engineered immune cell expressing the CAR of the present disclosure.

As used herein, the term "immune cell" refers to any cell of the immune system that has one or more effector functions (e.g., cytotoxic cell killing activity, secretion of cytokines, induction of ADCC and/or CDC). For example, the immune cell may be a T cell, a macrophage, a dendritic cell, a monocyte, an NK cell, and/or an NKT cell. In an embodiment, the immune cell is derived from a stem cell, such as an adult stem cell, an embryonic stem cell, a cord blood stem cell, a progenitor cell, a bone marrow stem cell, an induced pluripotent stem cell, a totipotent stem cell, or a hematopoietic stem cell, and so on. Preferably, the immune cell is a T cell. The T cell may be any T cell, such as in vitro cultured T cell, for example, primary T cell, or T cell from in vitro cultured T cell line, e.g., Jurkat, SupT1, etc., or T cell obtained from a subject. Examples of subject include humans, dogs, cats, mice, rats, and transgenic species thereof. The T cell can be obtained from a variety of sources, including peripheral blood monocytes, bone marrow, lymph node tissue, umbilical blood, thymus tissue, tissue from sites of infection, ascites, pleural effusion, spleen tissue, and tumors. The T cell also may be concentrated or purified. The T cell may be at any stage of development including, but not limited to, a CD4+/CD8+ T cell, a CD4+ helper T cell (e.g., Th1 and Th2 cells), CD8+ T cell (e.g., cytotoxic T cell), tumor infiltrating cell, memory T cell, naive T cell, γδ-T cell, αβ-T cell. In a preferred embodiment, the immune cell is a human T cell. The T cell can be isolated from the blood of a subject using a variety of techniques known to those of skill in the art, such as Ficoll.

The nucleic acid sequence encoding the chimeric antigen receptor can be introduced into an immune cell using conventional methods known in the art (e.g., by transduction, transfection, transformation). "Transfection" is a process of introducing a nucleic acid molecule or polynucleotide (including a vector) into a target cell. An example is RNA transfection, i.e., the process of introducing RNA (e.g., in vitro transcribed RNA, ivtRNA) into a host cell. This term is mainly used for a non-viral method in eukaryotic cells. The term "transduction" is generally used to describe virus-mediated transfer of nucleic acid molecules or polynucleotides. Transfection of animal cells typically involves opening transient pores or "holes" in the cell membrane, so as to allow uptake of material. Transfection may be carried out using calcium phosphate, by electroporation, by extrusion of cells, or by mixing cationic lipids with the material so as to produce liposomes which fuse with the cell membrane and deposit their cargo into the interior. Exemplary techniques for transfecting eukaryotic host cells include lipid vesicle-mediated uptake, heat shock-mediated uptake, calcium phosphate-mediated transfection (calcium phosphate/DNA co-precipitation), microinjection, and electroporation. The term "transformation" is used to describe the non-virus transfer of a nucleic acid molecule or polynucleotide (including a vector) to bacteria, and also to non-animal eukaryotic cells (including plant cells). Thus, the transformation is a genetic alteration of bacterial or non-animal eukaryotic cells, which is produced by direct uptake of a cell membrane from its surroundings and subsequent incorporation of exogenous genetic material (nucleic acid molecule). The transformation can be achieved by artificial means. In order for transformation to occur, the cell or bacterium must be in a competent state. For prokaryotic transformation, the techniques may include heat shock-mediated uptake, fusion to bacterial protoplasts of intact cells, microinjection, and electroporation. After the nucleic acid or vector is introduced into the immune cells, those skilled in the art can amplify and activate the obtained immune cells by conventional techniques.

In an embodiment, in order to reduce the risk of graft-versus-host disease, the engineered immune cell further comprises suppressed or silenced expression of at least one gene selected from the group consisting of: CD52, GR, dCK, TCR/CD3 genes (e.g., TRAC, TRBC, CD3γ, CD3δ, CD3ε, CD3ζ), MHC related genes (HLA-A, HLA-B, HLA-C, B2M, HLA-DPA, HLA-DQ, HLA-DRA, TAP1, TAP2, LMP2, LMP7, RFX5, RFXAP, RFXANK, CIITA) and immune checkpoint genes such as PD1, LAG3, TIM3, CTLA4, PPP2CA, PPP2CB, PTPN6, PTPN22, PDCD1, HAVCR2, BTLA, CD160, TIGIT, CD96, CRTAM, TNFRSF10B, TNI-RSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT, FOXP3, PRDM1, BATF, GUCY1A2, GUCY1A3, GUCY1B2 and GUCY1B3. Preferably, the engineered immune cell further comprises suppressed or silenced expression of at least one gene selected from the group consisting of: TRAC, TRBC, HLA-A, HLA-B, HLA-C, B2M, RFX5, RFXAP, RFXANK, CIITA, PD1, LAG3, TIM3, CTLA4, more preferably TRAC, TRBC, HLA-A, HLA-B, HLA-C, B2M, RFX5, RFXAP, RFXANK, CIITA.

Methods of inhibiting gene expression or silencing genes are well known to those skilled in the art. For example, antisense RNA, RNA decoys, RNA aptamers, siRNA, shRNA/miRNA, trans dominant negative protein (TNP), chimeric/antibody conjugates, chemokine ligands, anti-infective cellular proteins, intracellular antibodies (sFv), nucleoside analogs (NRTI), non-nucleoside analogs (NNRTI), integrase inhibitors (oligonucleotides, dinucleotides, and chemical agents), and protease inhibitors may be used to inhibit the expression of genes. Alternatively, genes can also be silenced by DNA fragmentation mediated by for example meganucleases, zinc finger nucleases, TALE nucleases or Cas enzymes in CRISPR systems.

In an embodiment, a plurality of immune cells is provided, each immune cell engineered to express one or more chimeric antigen receptors. For example, in some embodiments, an immune cell is engineered to express a chimeric antigen receptor that binds and/or targets CD7 (e.g., a CAR comprising the anti-CD7 humanized antibody of the present disclosure), and another cell is engineered to express a chimeric antigen receptor that binds and/or targets antigens different from CD7. In an embodiment, immune cells may also express multispecific chimeric antigen receptors that target one or more antigens, including CD7. For example, such a multispecific chimeric antigen receptor may comprise a multispecific antibody targeting CD7, or comprise both the anti-CD7 humanized antibody of the present disclosure and antibodies targeting antigens different from CD7. In such embodiments, the plurality of engineered immune cells may be administered together or separately. In an embodiment, the plurality of immune cells can be in the same composition or in different compositions. Exemplary compositions of cells include those described in the following sections of this application.

Antibody Conjugate

In an aspect, the present disclosure provides an antibody conjugate comprising the anti-CD7 humanized antibody as defined in the present disclosure and a second functional structure, wherein the second functional structure is selected from the group consisting of Fc, a radioisotope, a structure moiety for extending half-life, a detectable marker and a drug.

In an embodiment, the present disclosure provides an antibody conjugate comprising the anti-CD7 humanized antibody as defined in the present disclosure and Fc. As used herein, the term "Fc" is used to define the C-terminal region of an immunoglobulin heavy chain, and includes natural Fc and variant Fc. "Natural Fc" refers to a molecule or sequence comprising a non-antigen-binding fragment, whether monomeric or multimeric, produced by digestion of an intact antibody. The source of immunoglobulin from which natural Fc is produced is preferably of human origin. Natural Fc fragments are composed of monomeric polypeptides that can be linked as dimers or multimers through covalent linkages (e.g., disulfide bonds) and non-covalent linkages. Depending on the class (e.g., IgG, IgA, IgE, IgD, IgM) or subtype (e.g., IgG1, IgG2, IgG3, IgA1, IgGA2), natural Fc molecules have 1-4 intermolecular disulfide bonds between monomeric subunits. An example of a natural Fc is a disulfide-linked dimer produced by papain digestion of IgG (see Ellison et al. (1982), Nucleic Acids Res. 10:4071-9). The term "natural Fc" as used herein generally refers to monomeric, dimeric and multimeric forms. A "variant Fc" refers to an amino acid sequence that differs from that of a "natural" or "wild-type" Fc by virtue of at least one "amino acid modification" as defined herein, also referred to as an "Fc variant". Thus, "Fc" also includes single-chain Fc (scFc), i.e., a single-chain Fc consisting of two Fc monomers linked by a polypeptide linker, which is capable of naturally folding into a functional dimeric Fc region. In an embodiment, the Fc is preferably the Fc of a human immunoglobulin, more preferably the Fc of a human IgG1.

In an embodiment, the present disclosure provides an antibody conjugate comprising the anti-CD7 humanized antibody as defined in the present disclosure and a radioactive isotope. Examples of radioisotopes useful in the present disclosure include, but are not limited to, $At^{211}$, $I^{131}$, $I^{125}$, $Y^{90}$, $Re^{186}$, $Re^{188}$, $Sm^{153}$, $Bi^{212}$, $P^{32}$, $Pb^{212}$, $^{99m}Tc$, $^{123}I$, $^{18}F$, and $^{68}Ga$.

In an embodiment, the present disclosure provides an antibody conjugate comprising the anti-CD7 humanized antibody as defined in the present disclosure and a structure moiety for extending half-life selected from the group consisting of an albumin-binding structure of, a transferrin-binding structure, a polyethylene glycol molecule, a recombinant polyethylene glycol molecule, human serum albumin, a fragment of human serum albumin, and a polypeptide binding to human serum albumin (including antibody).

In an embodiment, the present disclosure provides an antibody conjugate comprising the anti-CD7 humanized antibody as defined in the present disclosure and a detectable marker. The term "detectable marker" means herein a compound that produces a detectable signal. For example, the detectable marker may be an MRI contrast agent, a scintigraphy contrast agent, an X-ray imaging contrast agent, an ultrasound contrast agent, an optical imaging contrast agent. Examples of detectable markers include fluorophores (e.g., fluorescein, Alexa, or cyanine), chemiluminescent compounds (e.g., luminol), bioluminescent compounds (e.g., luciferase or alkaline phosphatase), enzymes (e.g., horseradish peroxidase, glucose-6-phosphatase, β-galactosidase), antibiotics (e.g., kanamycin, ampicillin, chloramphenicol, tetracycline, etc.) resistance genes, and contrast agents (e.g., nanoparticles or gadolinium). Those skilled in the art can select an appropriate detectable marker according to the detection system used.

In an embodiment, the present disclosure provides an antibody conjugate comprising the anti-CD7 humanized antibody as defined in the present disclosure and a drug conjugated to the anti-CD7 humanized antibody, such as a cytotoxin or an immunomodulator (i.e., an antibody-drug conjugate). Usually, the drug is covalently linked to the antibody, usually by a linker. In an embodiment, the drug is a cytotoxin. In another embodiment, the drug is an immunomodulator. Examples of cytotoxins include, but are not limited to, methotrexate, aminopterin, 6-mercaptopurine, 6-thioguanine, cytarabine, 5-fluorouracil, dacarbazine, nitrogen mustard, thiotepa, chlorambucil, melphalan, carmustine (BSNU), lomustine (CCNU), 1-methylnitrosourea, cyclophosphamide, nitrogen mustard, busulfan, dibromomannitol, streptozocin, mitomycin, cis-dichlorodiamine platinum (II) (DDP), cisplatin, carboplatin, zorubicin, doxorubicin, detorubicin, carminomicin, idarubicin, epirubicin, mitoxantrone, actinomycin D, bleomycin, calicheamicin, mithramycin, antramycin (AMC), vincristine, vinblastine, paclitaxel, ricin, *pseudomonas* exotoxin, gemcitabine, cytochalasin B, gramicidin D, ethidium bromide, emetine, etoposide, teniposide, colchicine, mitoxantrone, 1-dehydrotestosterone, glucocorticoid, procaine, tetracaine, lidocaine, propranolol, puromycin, procarbazine, hydroxyurea, asparaginase, corticosteroids, mitotane (O,P'-(DDD)), interferon, and combinations thereof. Examples of immunomodulators include, but are not limited to, ganciclovir, etanercept, tacrolimus, sirolimus, voclosporin, cyclosporine, rapamycin, cyclophosphamide, azathioprine, mycophenolate mofetil, methotrexate, glucocorticoid and analogs thereof, cytokines, stem cell growth factors, lymphotoxins, tumor necrosis factor (TNF), hematopoietic factors, interleukins (e.g., IL-1, IL-2, IL-3, IL-6, IL-10, IL-12, IL-18 and IL-21), colony-stimulating factors (e.g., G-CSF and (GM-CSF), interferons (e.g., interferon-α, interferon-beta and interferon-gamma), stem cell growth factor designated "Si factor", erythropoietin and thrombopoietin, or combinations thereof.

Kits and Pharmaceutical Compositions

In another aspect, the present disclosure further provides a detection kit comprising the humanized antibody, the multispecific antibody, the antibody conjugate or the chimeric antigen receptor described in the present disclosure.

In another aspect, the present disclosure further provides a pharmaceutical composition comprising the humanized antibody, the chimeric antigen receptor, the multispecific antibody or the antibody conjugate of the present disclosure, and one or more pharmaceutically acceptable excipients.

As used herein, the term "pharmaceutically acceptable excipient" refers to a vector and/or excipient that is pharmacologically and/or physiologically compatible (i.e., capable of triggering a desired therapeutic effect without causing any undesired local or systemic effects) with the subject and active ingredient, and it is well known in the art (see, e.g., Remington's Pharmaceutical Sciences. Edited by Gennaro A R, 19$^{th}$ ed. Pennsylvania: Mack Publishing Company, 1995). Examples of pharmaceutically acceptable excipient include, but are not limited to, filler, binder, disintegrant, coating agent, adsorbent, anti-adherent, glidant, antioxidant, flavoring agent, colorant, sweetener, solvent, co-solvent, buffer agent, chelating agent, surfactant, diluent, wetting agent, preservative, emulsifier, cladding agent, isotonic agent, absorption delaying agent, stabilizer, and tension regulator. It is known to those skilled in the art to select a suitable excipient to prepare the desired pharmaceutical composition of the present disclosure. Exemplary excipients for use in the pharmaceutical composition of the present disclosure include saline, buffered saline, dextrose, and water. Generally, the selection of a suitable excipient depends, in particular, on the active agent used, the disease to be treated, and the desired dosage form of the pharmaceutical composition.

The pharmaceutical composition according to the present disclosure is suitable for multiple routes of administration. Generally, the administration is parenterally accomplished.

Parenteral delivery methods comprise topical, intraarterial, intramuscular, subcutaneous, intramedullary, intrathecal, intraventricular, intravenous, intraperitoneal, intrauterine, intravaginal, sublingual, or intranasal administration.

The pharmaceutical composition according to the present disclosure also can be prepared in various forms, such as solid, liquid, gaseous or lyophilized forms, particularly the pharmaceutical composition can be prepared in the form of ointment, cream, transdermal patch, gel, powder, tablet, solution, aerosol, granule, pill, suspension, emulsion, capsule, syrup, elixir, extract, tincture or liquid extract, or in a form particularly suitable for the desired method of administration. Processes known in the present disclosure for producing a medicine may include, for example, conventional mixing, dissolving, granulating, dragee-making, grinding, emulsifying, encapsulating, embedding or lyophilizing process. The pharmaceutical composition containing, for example, the immune cell as described herein is generally provided in a form of solution, and preferably contains a pharmaceutically acceptable buffer agent.

The pharmaceutical composition according to the present disclosure further may be administered in combination with one or more other agents suitable for the treatment and/or prophylaxis of diseases to be treated. Preferred examples of agent suitable for the combination include known anticancer medicines such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E, vincristine and doxorubicin; peptide cytotoxins, such as ricin, diphtheria toxin, *pseudomonas* exotoxin A, DNase and RNase; radionuclides such as iodine 131, rhenium 186, indium 111, iridium 90, bismuth 210, bismuth 213, actinides 225 and astatine 213; prodrugs such as antibody-directed enzyme prodrugs; immunostimulatory agents such as platelet factor 4, and melanoma growth stimulating protein; antibodies or fragments thereof, such as anti-CD3 antibodies or fragments thereof, complement activators, heterologous protein domains, homologous protein domains, viral/bacterial protein domains and viral/bacterial peptides. In addition, the pharmaceutical composition of the present disclosure also can be used in combination with one or more other treatment methods, such as chemotherapy and radiotherapy.

Therapeutic/Preventive/Diagnostic Use

In another aspect, the present disclosure further provides a method for treating and/or preventing and/or diagnosing diseases associated with CD7 expression, comprising administering to a subject the humanized antibody, the chimeric antigen receptor, the multispecific antibody, the antibody conjugate or the pharmaceutical composition as described above.

In an embodiment, diseases associated with CD7 expression include non-solid tumors (such as hematological tumors, e.g., leukemias and lymphomas) and solid tumors. Hematological neoplasms are cancers of the blood or bone marrow, including but not limited to acute leukemias (such as acute lymphoblastic leukemia, acute myeloid leukemia, acute myelogenous leukemia, and myeloblastic, promyelocytic, myelomonocytic, monocytic and erythroleukemia), chronic leukemia (such as chronic myeloid (granulocytic) leukemia, chronic myelogenous leukemia, and chronic lymphocytic leukemia), polycythemia vera, lymphoma, Hodgkin's lymphoma, non-Hodgkin's lymphoma (indolent and high-grade forms), multiple myeloma, Waldenstrom's macroglobulinemia, myelodysplastic syndrome, hairy cell leukemia, Burkitt's lymphoma, diffuse large cell lymphoma, mantle cell lymphoma, T-lymphoblastic leukemia/lymphoma (T-ALL/LBL), early pro-T-lymphoblastic leukemia (ETP-ALL), extranodal NK/T-cell lymphoma, small lymphocytic lymphoma (SLL) and myelodysplasia. Solid tumors are abnormal masses of tissue that usually do not contain cysts or areas of fluid, and can be benign or malignant. The different types of solid tumors are named according to the type of cells that form them (such as sarcomas, carcinomas, and lymphomas). Examples of solid tumors include, but are not limited to, fibrosarcoma, myxosarcoma, liposarcoma, mesothelioma, pancreatic cancer, ovarian cancer, peritoneal, omental, and mesenteric cancer, pharyngeal cancer, prostate cancer, rectal cancer, renal cancer, skin cancer, small intestine cancer, melanoma, kidney cancer, laryngeal cancer, soft tissue cancer, stomach cancer, testicular cancer, colon cancer, esophagus cancer, cervical cancer, alveolar rhabdomyosarcoma, bladder cancer, bone cancer, brain cancer, breast cancer, anal cancer, eye cancer, intrahepatic cholangiocarcinoma, joint cancer, neck cancer, gallbladder cancer, pleural cancer, nasal cancer, middle ear cancer, oral cancer, vulvar cancer, thyroid cancer and ureter cancer.

In an embodiment, the disease associated with CD7 expression is preferably selected from the group consisting of acute lymphoblastic leukemia (ALL), acute myeloid leukemia (AML), T-lymphoblastic lymphoma (T-LBL), early pro-T lymphoblastic Leukemia (ETP-ALL) and extranodal NK/T cell lymphoma.

The present disclosure will be described in detail below with reference to the accompanying drawings and examples. It should be noted that those skilled in the art should understand that the drawings and the embodiments of the present disclosure are only for the purpose of illustration, and shall not constitute any limitation to the present disclosure. In the case of no contradiction, the embodiments in the present application and the features in the embodiments can be combined with each other.

EXAMPLE

Figure 1:
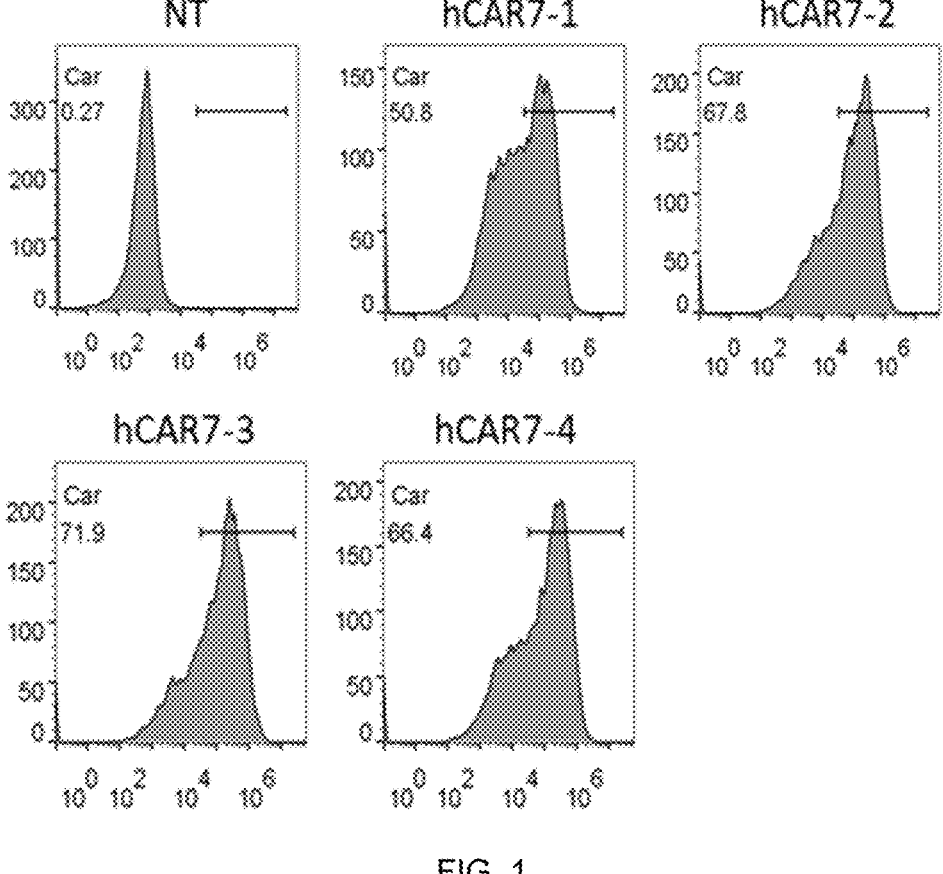
FIG. 1 shows the scFv expression levels of CAR-T cells containing anti-CD7 humanized antibody.

Example 1. Preparation of CD7 Humanized Antibodies

The humanized antibodies were prepared based on murine CD7 scFv (clone m189). Clone m189 comprises CDR-L1 as set forth in SEQ ID NO: 1, CDR-L2 as set forth in SEQ ID NO: 2, CDR-L3 as set forth in SEQ ID NO: 3, CDR-H1 as set forth in SEQ ID NO: 4, CDR-H2 as set forth in SEQ ID NO:5, CDR-H3 as set forth in SEQ ID NO:6, with an amino acid sequence as set forth in SEQ ID NO: 7. The specific method for preparing the humanized antibodies is as follows: first, sequence similarity search was carried out by Ig BLAST (http://www.ncbi.nlm nih.gov/igblast/) and IMGT (Immune Gene Database IMGT: http://www.imgt.org), and in the search results, antibodies with high sequence similarity to both light and heavy chains were selected as humanized antibody templates. Then, the heavy chain CDR and light chain CDR in the murine CD7 scFv were grafted into the framework of the humanized antibody template with high sequence similarity, and then reverse mutation was performed to ensure the affinity and specificity of the humanized antibody. The final amino acid sequence of CD7 humanized single-chain antibody (scFv) is shown in Table 1 below.

TABLE 1

| Sequences of humanized CD7 scFvs | | | |
| --- | --- | --- | --- |
| | h189-1 | h189-2 | h189-3 | h189-4 |
| VL (aa) | SEQ ID NO: 8 | SEQ ID NO: 11 | SEQ ID NO: 14 | SEQ ID NO: 17 |
| VH (aa) | SEQ ID NO: 9 | SEQ ID NO: 12 | SEQ ID NO: 15 | SEQ ID NO: 18 |
| scFv (aa) | SEQ ID NO: 10 | SEQ ID NO: 13 | SEQ ID NO: 16 | SEQ ID NO: 19 |
| scFv (nt) | SEQ ID NO: 20 | SEQ ID NO: 21 | SEQ ID NO: 22 | SEQ ID NO:23 |

Example 2. Preparation of CAR-T Cells Containing Anti-CD7 Humanized Antibody

Sequences encoding the following proteins were synthesized and cloned into pLVX vector (Public Protein/Plasmid Library (PPL), Cat. No.: PPL00157-4a): CD8a signal peptide (SEQ ID NO: 38), CD7 humanized scFv (selected from SEQ ID NO: 10, 13, 16, 19), CD8a hinge region (SEQ ID NO: 40), CD8a transmembrane region (SEQ ID NO: 24), 4-1BB intracellular region (SEQ ID NO: 30) and CD3 intracellular signaling domain (SEQ ID NO: 32), and the correct insertion of the target sequence was confirmed by sequencing. The amino acid sequence of the anti-CD7 scFv contained in the hCAR7-1 CAR is set forth in SEQ ID NO: 10; the amino acid sequence of the anti-CD7 scFv contained in the hCAR7-2 CAR is set forth in SEQ ID NO: 13; the amino acid sequence of the anti-CD7 scFv contained in the hCAR7-3 CAR is set forth in SEQ ID NO: 16; the amino acid sequence of the anti-CD7 scFv contained in the hCAR7-4 CAR is set forth in SEQ ID NO: 19.

Three ml Opti-MEM (Gibco, Cat. No. 31985-070) was added to a sterile tube to dilute the above plasmid, and then packaging vector psPAX2 (Addgene, Cat. No. 12260) and envelope vector pMD2.G (Addgene, Cat. No. 12259) were added according to the ratio of plasmid:viral packaging vector:viral envelope vector=4:2:1. Then, 120 µl X-treme GENE HP DNA transfection reagent (Roche, Cat. No. 06366236001) was added, mixed immediately, and incubated at room temperature for 15 min, and then the plasmid/vector/transfection reagent mixture was added dropwise to the culture flask of 293T cells. Viruses were collected at 24 hours and 48 hours, pooled, and ultracentrifuged (25000 g, 4° C., 2.5 hours) to obtain concentrated lentiviruses.

Since CD7 is also expressed on T cells, in order to avoid mutual killing between CAR-T cells, the inventor knocked out CD7 in T cells through the CRISP/Cas9 system. After 1 day of culture, T cells were activated with DynaBeads CD3/CD28 CTS™ (Gibco, Cat. No. 40203D), and were further cultured for 1 day at 37° C. and 5% CO 2. Then, the concentrated lentivirus was added, and after 3 days of continuous culture, CAR T cells expressing different CD7 humanized scFv were obtained. Unmodified wild-type T cells were used as negative controls (NT).

The expression level of scFv on the hCAR7-1 T cells, hCAR7-2 T cells, hCAR7-3 T cells and hCAR7-4 cells was detected by flow cytometry using Biotin-SP (long spacer) AffiniPure Goat Anti-Mouse IgG, F(ab')2 Fragment Specific (min X Hu, Bov, Hrs Sr Prot) (Jackson immunoresearch, Cat. No. 115-065-072) as the primary antibody, APC Streptavidin (BD Pharmingen, Cat. No. 554067) or PE Streptavidin (BD Pharmingen, Cat. No. 554061) as the secondary antibody, and the results are shown in FIG. 1.

It can be seen that the CD7 humanized scFv in the CAR T cells prepared by the present disclosure can be effectively expressed.

Example 3. Killing Effect of CAR T Cells on Target Cells and Release of Cytokines 3.1 The Killing Effect of CAR-T Cells on Target Cells When T cells kill target cells, the number of target cells will decrease. After co-culturing T cells with target cells expressing luciferase, the number of target cells decreases and the secretion of luciferase decreases accordingly. Luciferase can catalyze the conversion of luciferin into oxidized luciferin, and during this oxidation process, bioluminescence will be generated, and the intensity of this luminescence will depend on the level of luciferase expressed by the target cells. Therefore, the detected fluorescence intensity can reflect the ability of T cells to kill target cells.

Figure 2:
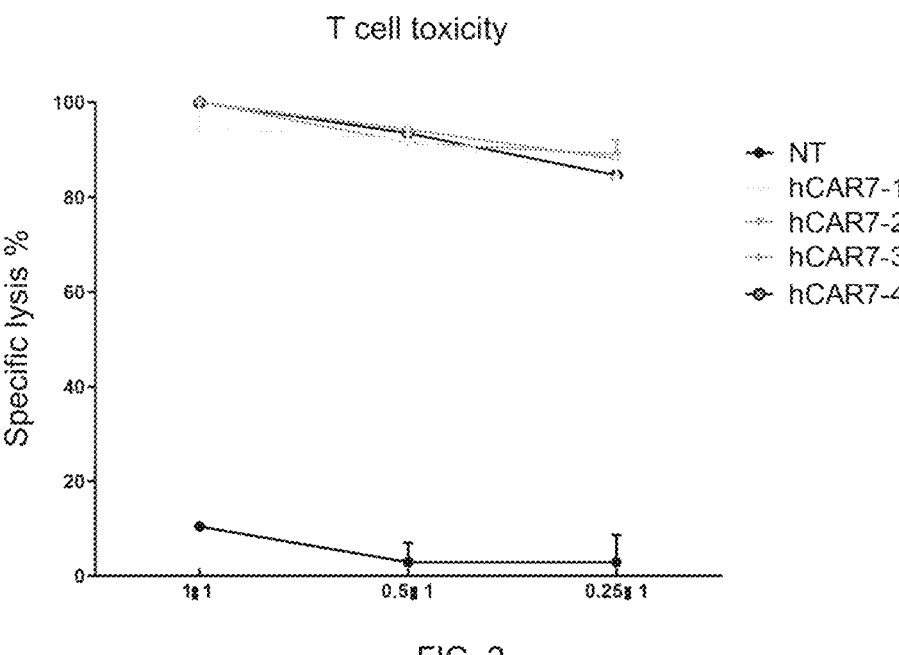
FIG. 2 shows the killing effect of CAR-T cells containing CD7 humanized antibodies on target cells.

In order to detect the killing ability of CAR-T cells on target cells, first Jurkat target cells carrying the fluorescein gene were plated into a 96-well plate at $1 \times 10^4$/well, and then CAR T cells and NT cells were plated in the 96-well plate with effector-target ratios (i.e., the ratio of effector T cells to target cells) of 1:1, 0.5:1 and 0.25:1 for co-culture, and the fluorescence value was measured with a microplate reader after 16-18 hours. According to the calculation formula: (average fluorescence value of target cells−average fluorescence value of samples)/average fluorescence value of target cells×100%, the killing efficiency was calculated, and the results are shown in FIG. 2.

It can be seen that, compared with NT, the CAR T cells of the present disclosure can specifically kill target cells.

3.2 Cytokine Release of CAR-T Cells

When T cells kill target cells, the number of target cells decreases and cytokines are released at the same time. According to the following steps, enzyme-linked immunosorbent assay (ELISA) was used to measure the release level of cytokine IFNγ when the CAR T cells of the present disclosure kill target cells.

(1) Collection of Cell Co-Culture Supernatant

Target cells were plated in a 96-well plate at a concentration of $1 \times 10^5$/well, and then CAR T cells and NT cells were co-cultured with target cells at a ratio of 1:1, and the cell co-culture supernatant was collected after 18-24 hours.

(2) Detection of the Secretion of IL-2 and IFN-γ in the Supernatant by ELISA

Figure 3:
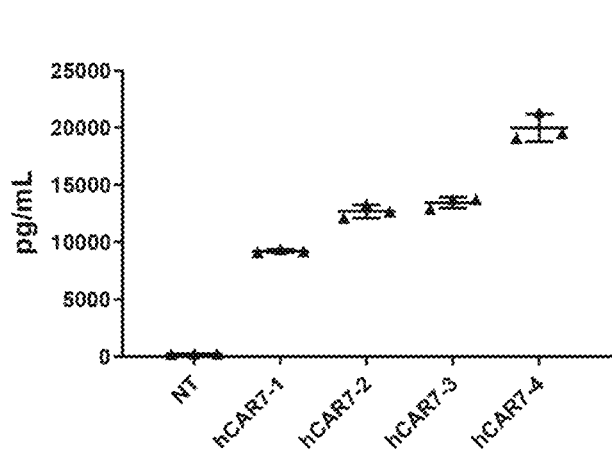
FIG. 3 shows the cytokine release level after co-culture of CAR-T cells containing anti-CD7 humanized antibody and target cells.

A 96-well plate was coated with Purified anti-human IFN-γ Antibody (Biolegend, Cat. No. 506502) as capture antibody and incubated overnight at 4° C., and then the antibody solution was removed. 250 µL of PBST (1×PBS containing 0.1% Tween) solution containing 2% BSA (sigma, Cat. No. V900933-1 kg) was added, and incubated at 37° C. for 2 hours. The plate was then washed 3 times with 250 µL PBST (1×PBS containing 0.1% Tween). 50 µL of cell co-culture supernatant or standard per well was added and incubated at 37° C. for 1 h, then the plate was washed 3 times with 250 µL of PBST (1×PBS containing 0.1% Tween). Then 50 µL Anti-Interferon gamma antibody [MD-1] (Biotin) (abcam, Cat. No. ab25017) as detection antibody was added to each well, incubated at 37° C. for 1 hour, and the plate was washed 3 times with 250 µL PBST (1×PBS containing 0.1% Tween). Then HRP Streptavidin (Bioleg-end, Cat. No. 405210) was added, incubated at 37° C. for 30 minutes, and the supernatant was discarded. 250 µL PBST (1×PBS containing 0.1% Tween) was added for washing 5 times. 50 µL of TMB substrate solution was added to each well. Reactions were allowed to occur at room temperature in the dark for 30 minutes, after which 50 µL of 1 mol/L $H_2SO_4$ was added to each well to stop the reaction. Within 30 minutes of stopping the reaction, a microplate reader was used to detect the absorbance at 450 nm, and the content of cytokines was calculated according to the standard curve (drawn according to the reading value and concentration of the standard), the results are shown in FIG. 3.

It can be seen that the cytokine release rate of the CAR T cells of the present disclosure is significantly higher than that of the control NT cells.

It should be noted that the above-mentioned are merely for preferred examples of the present disclosure and not used to limit the present disclosure. For one skilled in the art, various modifications and changes may be made to the present disclosure. Those skilled in the art should understand that any amendments, equivalent replacements, improvements, and so on, made within the spirit and principle of the present disclosure, should be covered within the scope of protection of the present disclosure.

---

What is claimed is:

1. An anti-CD7 humanized antibody comprising a light chain variable region and a heavy chain variable region, wherein the light chain variable region comprises CDR-L1 as set forth in SEQ ID NO: 1, CDR-L2 as set forth in SEQ ID NO: 2 and CDR-L3 as set forth in SEQ ID NO: 3, the heavy chain variable region comprises CDR-H1 as set forth in SEQ ID NO: 4, CDR-H2 as set forth in SEQ ID NO: 5 and CDR-H3 as set forth in SEQ ID NO: 6, and the light chain variable region has at least 90% sequence identity to an amino acid sequence selected from the group consisting of SEQ ID NOs: 8, 11, 14 and 17, and the heavy chain variable region has at least 90% sequence identity to an amino acid sequence selected from the group consisting of SEQ ID NOs: 9, 12, 15 and 18.

2. The humanized antibody according to claim 1, wherein the anti-CD7 humanized antibody comprises a light chain variable region-consisting of SEQ ID NO: 17 and a heavy chain variable region consisting of SEQ ID NO: 18.

3. The humanized antibody according to claim 1, wherein the anti-CD7 humanized antibody has an amino acid sequence selected from the group consisting of SEQ ID NOs: 10, 13, 16 and 19.

4. A multispecific antibody comprising the humanized antibody according to claim 1 and one or more second antibodies or antigen-binding portions thereof that specifically bind to antigens different from CD7.

5. The multispecific antibody according to claim 4, wherein the second antibody or antigen binding portion thereof is selected from the group consisting of a full-length antibody, Fab, Fab', (Fab')2, Fv, scFv, scFv-scFv, a mini-body, a diabody or sdAb.

6. An antibody conjugate comprising the humanized antibody according to claim 1, and a second functional structure, wherein the second functional structure is selected from the group consisting of Fc, a radioisotope, a structure moiety for extending half-life, a detectable marker and a drug.

7. A detection kit, comprising the humanized antibody according to claim 1.

8. A pharmaceutical composition, comprising the humanized antibody according to claim 1, and one or more pharmaceutically acceptable excipients.

9. The humanized antibody according to claim 1, wherein the anti-CD7 humanized antibody comprises:

a light chain variable region as set forth in SEQ ID NO: 8 and a heavy chain variable region as set forth in SEQ ID NO: 9;

a light chain variable region as set forth in SEQ ID NO: 11 and a heavy chain variable region as set forth in SEQ ID NO: 12; or a light chain variable region as set forth in SEQ ID NO: 14 and a heavy chain variable region as set forth in SEQ ID NO: 15.

* * * * *